United States Patent
Venkataramani et al.

(10) Patent No.: US 10,307,141 B2
(45) Date of Patent: Jun. 4, 2019

(54) THERMOGRAPHY-BASED BREAST CANCER SCREENING USING A MEASURE OF SYMMETRY

(71) Applicant: Niramai Health Analytix Pvt. Ltd., Bangalore (IN)

(72) Inventors: Krithika Venkataramani, Bangalore (IN); Susmija Jabbireddy, Hyderabad (IN); Himanshu J. Madhu, Mumbai (IN); Siva Teja Kakileti, Kakinada (IN); Hadonahalli V. Ramprakash, Bangalore (IN)

(*) Notice: Subject to any disclaimer, the term of this patent is extended or adjusted under 35 U.S.C. 154(b) by 36 days.

(21) Appl. No.: 15/636,718

(22) Filed: Jun. 29, 2017

(65) Prior Publication Data

US 2018/0000461 A1 Jan. 4, 2018

Related U.S. Application Data

(60) Provisional application No. 62/356,176, filed on Jun. 29, 2016.

(51) Int. Cl.
 *G06K 9/00* (2006.01)
 *A61B 10/00* (2006.01)
 (Continued)

(52) U.S. Cl.
 CPC ........ *A61B 10/0041* (2013.01); *A61B 5/0033* (2013.01); *A61B 5/015* (2013.01);
 (Continued)

(58) Field of Classification Search
 None
 See application file for complete search history.

(56) References Cited

U.S. PATENT DOCUMENTS 4,428,382 A * 1/1984 Walsall .................. A61B 5/015
 600/549
9,486,146 B2 * 11/2016 Venkataramani ....... G06T 7/136
 (Continued)

FOREIGN PATENT DOCUMENTS

WO 2004080298 * 9/2014 ............. A61B 5/015

OTHER PUBLICATIONS

Kuruganti et al ("Asymmetry Analysis in Breast Cancer Detection Using Thermal Infrared Images", Proceedings 01 the Second Joint EMBSiBMES Conference Houston, TX USA *Oct. 23-26, 2002).*
(Continued)

*Primary Examiner* — Shervin K Nakhjavan
(74) *Attorney, Agent, or Firm* — The Law Office Of Austin Bonderer, PC; Austin Bonderer

(57) ABSTRACT

What is disclosed is a system and method for breast cancer screening which determines whether hot spots, as seen in a thermal image of both breasts, can be classified as possibly malignant based on a measure of symmetry. A thermographic image of both breasts of a patient is received and analyzed to determine whether there exists, in each of a left breast and a right breast, a hot spot comprising a patch of pixels with an elevated temperature with respect to surrounding tissue. If a hot spot has been identified in each breast then a measure of symmetry comprising a ratio of an area of a smaller hot spot to an area of a larger hot spot is extracted from the thermographic image. The measure of symmetry is provided to a classifier system trained to classify an unclassified hot spot as malignant or non-malignant based on a measure of symmetry.

19 Claims, 7 Drawing Sheets

(51) Int. Cl.
  *A61B 5/00*    (2006.01)
  *A61B 5/01*    (2006.01)
  *G06T 7/00*    (2017.01)
  *G06T 7/68*    (2017.01)

(52) U.S. Cl.
  CPC .......... *A61B 5/4312* (2013.01); *G06T 7/0014* (2013.01); *G06T 7/68* (2017.01); *A61B 5/0013* (2013.01); *A61B 2562/0276* (2013.01); *A61B 2576/02* (2013.01); *G06T 2207/10048* (2013.01); *G06T 2207/30068* (2013.01)

(56) References Cited

U.S. PATENT DOCUMENTS

| | | | |
|---|---|---|---|
| 10,055,542 B2* | 8/2018 | Venkataramani | G06F 19/321 |
| 10,068,330 B2* | 9/2018 | Parthasarathy | G06T 7/13 |
| 2004/0181375 A1* | 9/2004 | Szu | A61B 5/7267 |
| | | | 703/2 |
| 2010/0312136 A1* | 12/2010 | Cozzie | A61B 5/015 |
| | | | 600/549 |
| 2016/0135686 A1* | 5/2016 | Gencer | A61B 5/0093 |
| | | | 600/474 |
| 2016/0283658 A1* | 9/2016 | Venkataramani | G06F 19/321 |

OTHER PUBLICATIONS

Borchartt et al ("Breast thermography from an image processing viewpoint: A survey", Signal Processing, vol. 93, Issue 10, Oct. 2013, pp. 2785-2803).*

* cited by examiner

THERMOGRAPHY-BASED BREAST CANCER SCREENING USING A MEASURE OF SYMMETRY

TECHNICAL FIELD

The present invention is directed to systems and methods for breast cancer screening which determines whether hot spots, as seen in a thermal image of both breasts, can be classified as being possibly malignant based on a determined measure of symmetry.

BACKGROUND

Breast cancer is one of the highest incidences among cancers in women. Breast cancer also has wide variations in the clinical and pathological features, which are taken into account for treatment planning, and to predict survival rates or treatment outcomes. Thermography is being used for breast imaging with the advent of high resolution thermal cameras. Thermography offers a radiation free and non-contact approach to breast imaging unlike the typically used mammography, which uses X-rays that have a risk of causing cancer if used frequently and is painful due to a lot of pressure used in breast compression. Thermography is also invariant to breast density unlike mammography which has a low sensitivity to breast cancer detection in women with dense breast tissues. Thermography detects the temperature increase in malignancy due to the increased metabolism of cancer and due to the additional blood ow generated for feeding the malignant tumors. The present invention is directed to this ongoing effort.

Accordingly, what is needed in this art are sophisticated systems and methods for breast cancer screening which determines whether hot spots, as seen in a thermal image of both breasts, can be classified as being possibly malignant based on a determined measure of symmetry.

BRIEF SUMMARY

What is disclosed is a system and method for breast cancer screening which determines whether hot spots, as seen in a thermal image of both breasts, can be classified as being possibly malignant based on a determined measure of symmetry. In one embodiment, at least one thermographic image of a left breast and a right breast of a patient undergoing breast cancer screening is received for processing. The thermographic image is analyzed to determine whether a hot spot exists in each of a left breast and a right breast. A hot spot is a patch of pixels with an elevated temperature with respect to a temperature of pixels in surrounding tissue. A temperature of a hot spot can be based on a mean temperature of pixels in the patch, a median temperature of pixels in the patch, and a highest temperature of pixels in the patch. If a hot spot has been identified in each breast then a measure of symmetry is extracted from the thermographic image. In one embodiment, the measure of symmetry comprises a ratio of an area of a smaller hot spot in one breast to an area of a larger hot spot in a contralateral breast. In another embodiment, the measure of symmetry additionally comprises a difference between an area of the larger hot spot and the area of the smaller hot spot. The measure of symmetry is provided to a classifier system trained to classify an unclassified hot spot as being possibly malignant and non-malignant otherwise.

Features and advantages of the above-described method will become readily apparent from the following detailed description and accompanying drawings.

BRIEF DESCRIPTION OF THE DRAWINGS

The foregoing and other features and advantages of the subject matter disclosed herein will be made apparent from the following detailed description taken in conjunction with the accompanying drawings, in which.

DETAILED DESCRIPTION

What is disclosed is a system and method for breast cancer screening which determines whether hot spots, as seen in a thermal image of both breasts, can be classified as being possibly malignant based on a determined measure of symmetry.

Non-Limiting Definitions

A "patient" refers to either a male or a female person. Gender pronouns are not to be viewed as limiting the scope of the appended claims strictly to females. Moreover, although the terms "subject", "person" or "patient" are used interchangeably throughout this disclosure, it should be appreciated that the patient undergoing cancer screening may be something other than a human such as, for example, a primate. Therefore, the use of such terms is not to be viewed as limiting the scope of the appended claims to humans.

Figure 1:
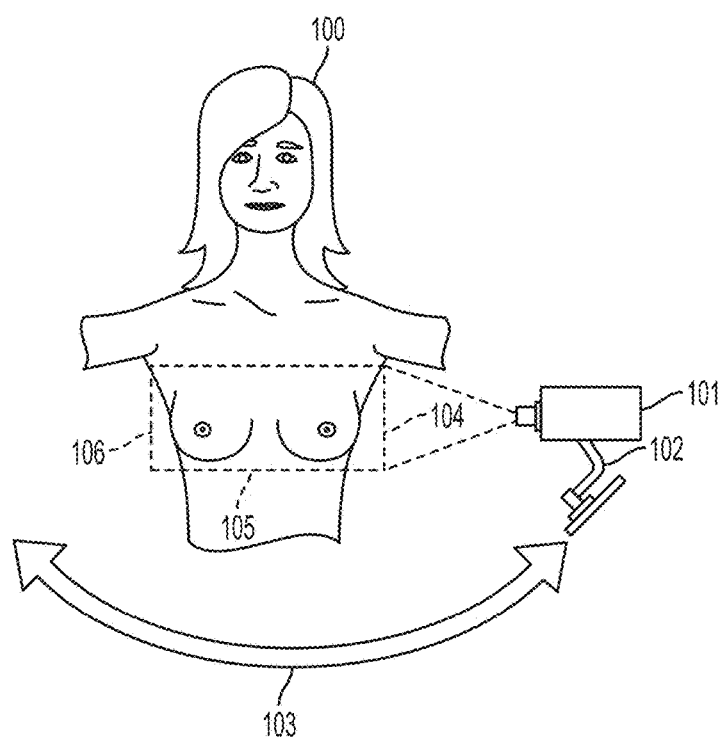
FIG. 1 shows an example female patient with a thermal camera mounted on a slideable and axially rotatable robotic arm for moving the camera along a semi-circular trajectory from side-to-side in front of the patient.

A "thermal camera" refers to either a still camera or a video camera with a lens that focuses infrared energy from objects in a scene onto an array of specialized sensors which convert infrared energy into electrical signals on a per-pixel basis and outputs a thermal image comprising an array of pixels with color values corresponding to temperatures of the objects in the image across a desired thermal wavelength band. FIG. 1 shows a thermal camera 101 mounted on a slideable and axially rotatable robotic arm 102 capable of moving the camera along a semi-circular trajectory 103 in the front of the patient from side-to-side such that thermographic images can be captured in a right-side view 104, a front view 105, and a left-side view 106, and various oblique angles in between. The thermal camera can be any of: a single-band infrared camera, a multi-band infrared camera in the thermal range, and a hyperspectral infrared camera in the thermal range. The resolution for a thermal camera is effectively the size of the pixel. Smaller pixels mean that more pixels will go into the thermal image giving the resulting image higher resolution and thus better spatial definition. Although thermal cameras offer a relatively large dynamic range of temperature settings, it is preferable that the camera's temperature range be relatively small, centered around the person's body surface temperature so that small temperature variations are amplified in terms of pixel color changes to provide a better measure of temperature variation. Thermal cameras are readily available in various streams of commerce. In one embodiment, the thermal camera is placed in wired or wireless communication with a workstation which enables manual or automatic control of various aspects of the thermal camera such as, for instance, adjusting a focus of the thermal camera lens, changing a resolution of the thermal camera, and changing a zoom level of the thermal camera.

Figure 2:
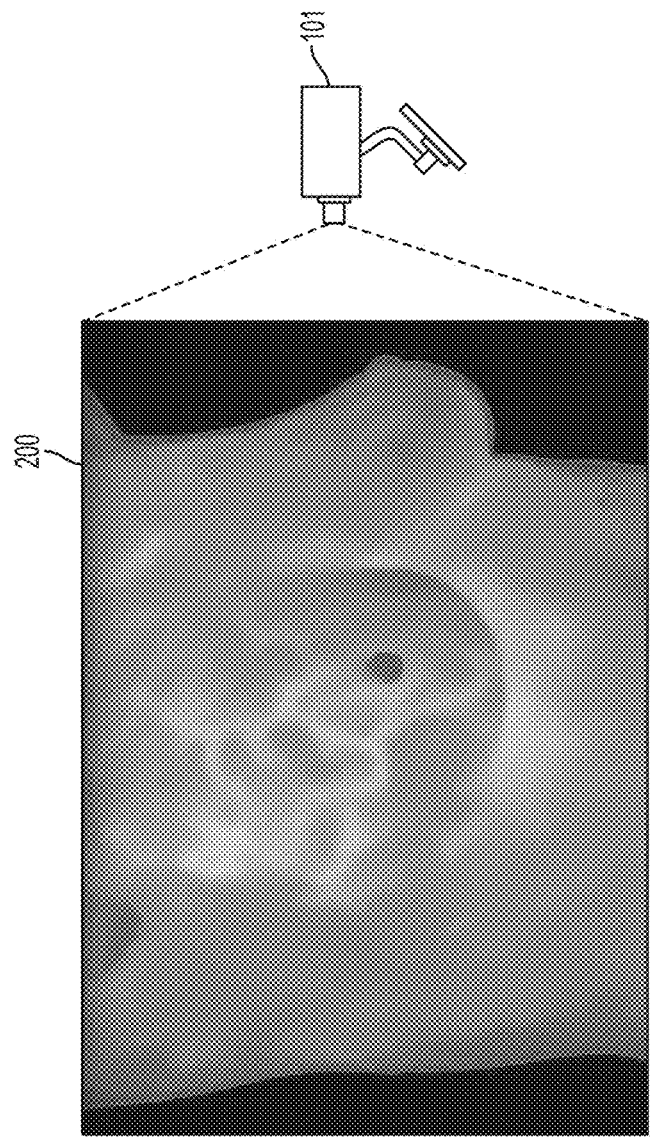
FIG. 2 shows a thermal image of an oblique view of a breast area of a female.

A "thermographic image" or simply "thermal image" comprises a plurality of pixels with each pixel having an associated corresponding temperature value. Pixels in the thermal image with a higher temperature value being displayed in a first color and pixels with a lower temperature value are displayed in a second color. Pixels with temperature values between the lower and higher temperature values are displayed in gradations of color between the first and second colors. FIG. 2 shows a thermal image 200 of an oblique view of a breast area. Although shown in black/white, it should be appreciated that the thermal image is a color image. Thermal images can be retrieved from a memory or storage device of the thermal imaging device, or obtained from a remote device over a network. Thermal images may be retrieved from a media such as a CDROM or DVD. Thermal images may be downloaded from a web-based system which makes such images available for processing. Thermal images can also be retrieved using an application such as those which are widely available for handheld cellular devices and processed on the user's cellphone or other handheld computing device such as an iPad or tablet. Use of the term "image" is intended to also mean "video". This thermal image can also be stored and retrieved purely as a two-dimensional matrix of real numbered values (also known as radiometric image) which are derived as a function of the measured temperature values that are represented by the color of each pixel in the thermal image.

"Receiving a thermal image" of a patient for cancer screening is intended to be widely construed and includes retrieving, capturing, acquiring, or otherwise obtaining video image frames. The image can be received or retrieved from a remote device over a network, or from a media such as a CDROM or DVD. The image may be downloaded from a web-based system or application which makes video available for processing in accordance with the methods disclosed herein. The image can also be received from an application such as those which are available for handheld cellular devices and processed on the cellphone or other handheld computing device such as an iPad or Tablet-PC. The image can be received directly from a memory or storage device of the imaging device used to capture that image or video. The received thermal image is analyzed to determine whether a hot spot exists in each of the left and right breasts in the thermal image.

Figure 3:
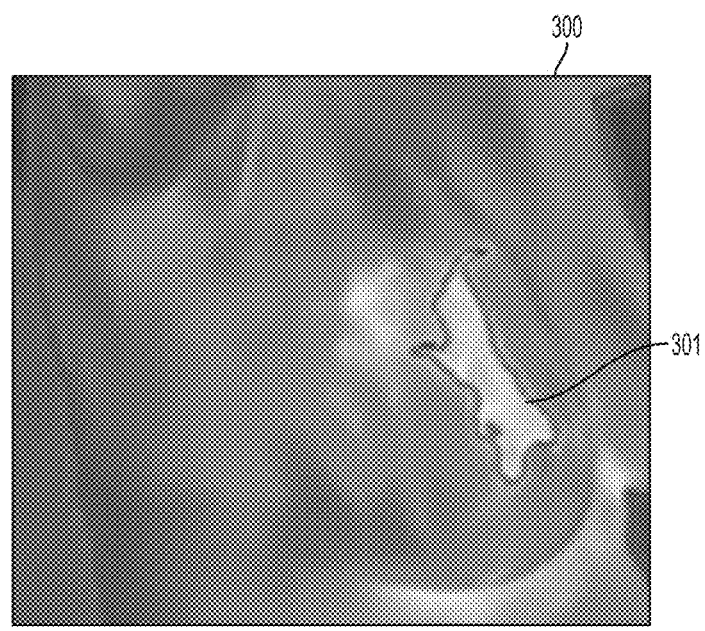
FIG. 3 shows a thermal image of a left breast wherein a hot spot comprising a patch of pixels with an elevated temperature is identified for analysis.
Figure 4:
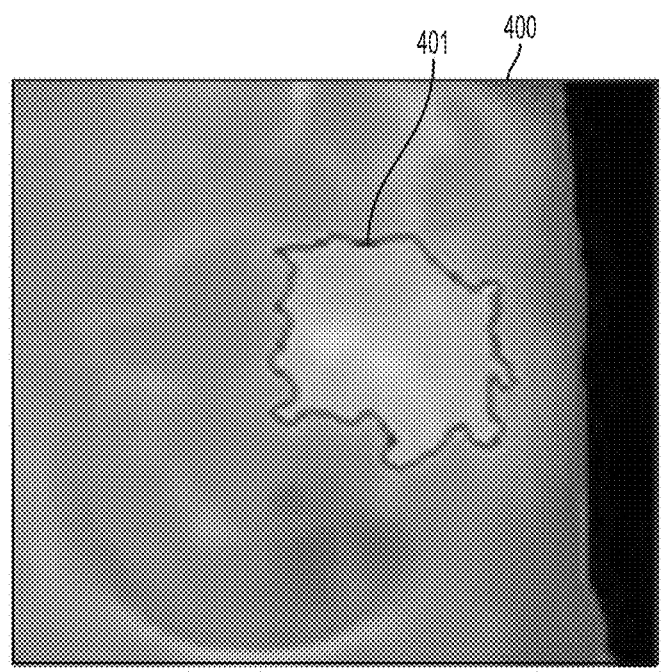
FIG. 4 shows a thermal image of a right breast wherein a hot spot comprising a patch of pixels with an elevated temperature is identified for analysis.

A "hot spot" is a patch of pixels with an elevated temperature relative to a temperature of pixels associated with surrounding tissue. FIG. 3 shows a thermal image 300 of a left breast wherein a hot spot 301 has been identified. FIG. 4 shows a thermal image 400 of a right breast wherein a hot spot 401 has been identified. Hot spots may be manually or automatically selected in the thermal image using, for example, temperatures of the isotherms of the thermal image or by a user making the selection. A hots pot inclusion status of a given patch of pixels can be based on a mean temperature of pixels in the patch, a median temperature of pixels in the patch, and a highest temperature of pixels in the patch. Hot spots in the thermographic image are analyzed to determine a measure of symmetry.

A patch of pixels may be called as a warm spot if they do not meet the inclusion criteria to be included in a hot spot, and are at a higher temperature than the rest of the breast. In addition to the hot spot, one or more warm spots are identified as potential abnormal elements that require attention. The potential abnormal elements comprise information for classifying the hot spot as possibly malignant.

Figure 5:
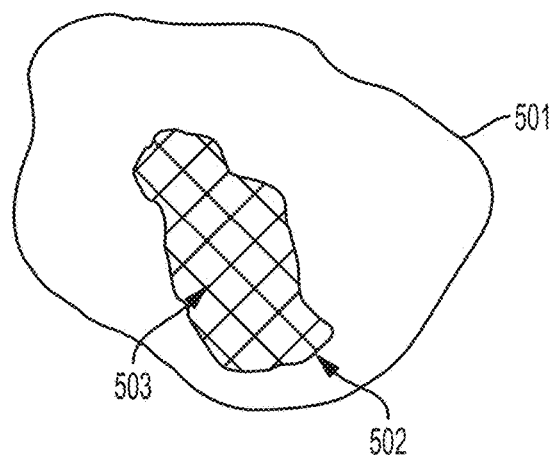
FIGS. 5 and 6 show an overlay of an example larger hot spot and an example smaller hot spot.
Figure 6:
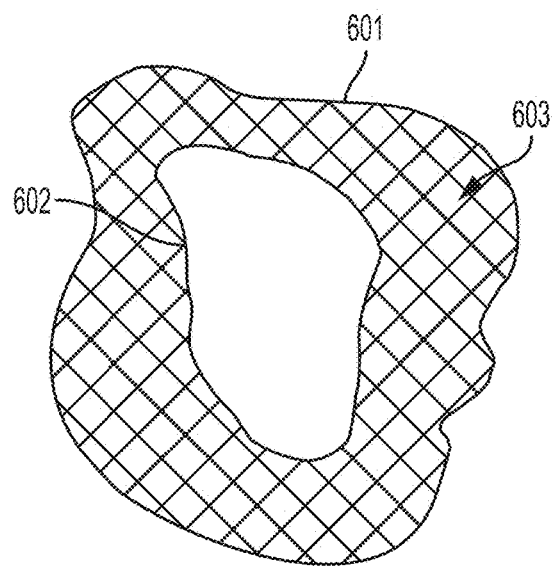

A "measure of symmetry", in one embodiment, is based on a ratio of an area of a smaller hot spot to an area of a larger hot spot in a contralateral breast. An area of a given patch of pixels can be determined in a variety of ways including, for example, a number of pixels in the hot spot which have the elevated temperature, or which have a temperature that is within a threshold range as determined by a medical practitioner given the patient's medical/family history. FIG. 5 shows an overlay of an example larger hot spot 501 identified, for example, in a left breast and an example smaller hot spot 502 identified in the right breast. FIG. 5 at 503 shows the extent of the area that the two hot spots have in common. FIG. 6 shows an overlay of an example larger hot spot 601 identified in a right breast and an example smaller hot spot 602 identified in the left breast. The measure of symmetry is provided to a classifier system.

A "classifier system" or simply "classifier" comprises at least a processor and a memory with the processor retrieving machine readable program instructions from memory and executing those instructions causing the processor to classify a measure of symmetry determined between a hot spot in one breast and a hot spot in a contralateral breast into at least a first or a second class based on a measure of symmetry, as defined herein. In a first class, the hot spots are classified as being possibly malignant. In a second class, the hot spots are classified as being non-malignant. The classifier is training using a training set which, in various embodiments, comprises patient medical records and historical data. By analyzing the training set, the classifier sets a threshold value. Once trained, the classifier then utilizes the threshold for classification. The threshold can be user adjusted or user manipulated as needed to minimize false positives and/or false negatives. As new data sets or additional parameters are added to the training set used to train the classifier, the threshold or decision boundary used by the classifier will likely change accordingly. Classifiers can take any of a variety of forms including a Support Vector Machine (SVM), a neural network, a Bayesian network, a Logistic Regression, Naïve Bayes, Randomized Forests, Decision Trees and Boosted Decision Trees, K-nearest neighbor, and a Restricted Boltzmann Machine (RBM), as are understood in the machine learning arts. For an in-depth discussion, the reader is directed to any of a wide variety of texts on classifiers, including: "*Foundations of Machine Learning*", MIT Press (2012), ISBN-13: 978-0262018258, and "*Design and Analysis of Learning Classifier Systems: A Probabilistic Approach*", Springer (2008), ISBN-13: 978-3540798651.

It should be appreciated that the steps of "receiving", "analyzing", "communicating", "performing", "determining", "selecting", "providing", "extracting" and the like, as used herein, include the application of any of a variety of techniques as well as mathematical operations according to any specific context or for any specific purpose. Such steps may be facilitated or otherwise effectuated by a microprocessor executing machine readable program instructions such that the intended functionality is effectively performed.

Flow Diagram of One Embodiment

Figure 7:
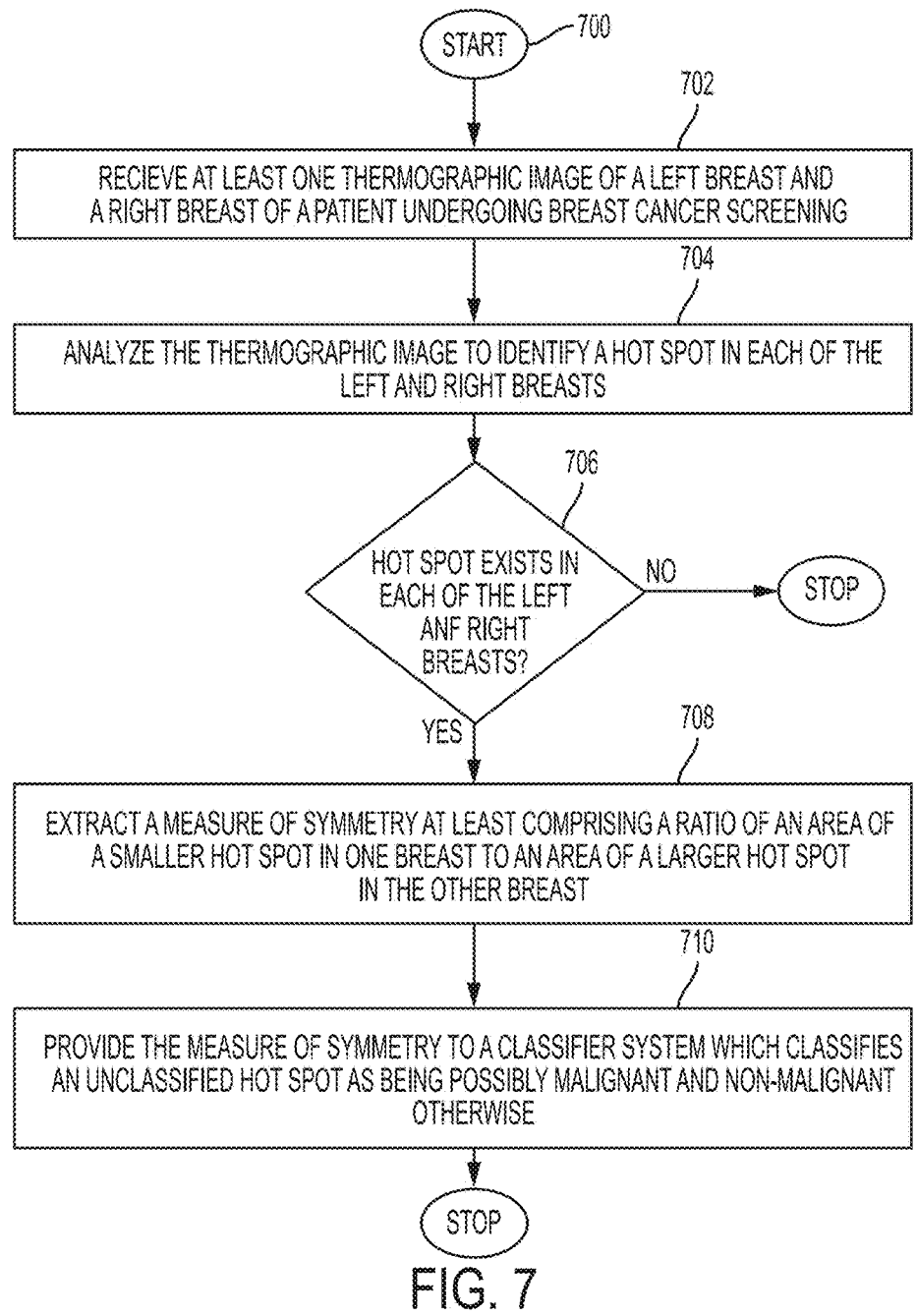
FIG. 7 is a flow diagram which illustrates one embodiment of the present method for breast cancer screening using a thermographic image of both breasts in accordance with the methods disclosed herein.

Reference is now being made to the flow diagram of FIG. 7 which illustrates one embodiment of the present method for breast cancer screening using a thermographic image of both breasts of a patient. Flow processing begins at step 700 and immediately proceeds to step 702.

At step 702, receive at least one thermographic image of a left breast and a right breast of a patient undergoing breast cancer screening. The thermographic image can be a single image of both breasts or separate images of each of the left and right breast.

At step 704, analyze the thermographic image to identify a hot spot in each of the left and right breasts. Example hot spots are shown in FIGS. 3 and 4.

At step 706, a determination is made whether a hot spot exists in each of the left and right breasts. If not, in this embodiment, further processing stops.

At step 708, extract a measure of symmetry at least comprising a ratio of an area of a smaller hot spot in one breast to an area of a larger hot spot in the other breast. Areas of overlap and non-overlap are shown and discussed with respect to FIGS. 5 and 6.

At step 710, provide the measure of symmetry to a classifier system which classifies an unclassified hot spot as being possibly malignant and non-malignant otherwise. In this embodiment further processing stops. It should be appreciated that other steps may be undertaken by a medical professional in response to the classification (malignant or non-malignant) as the medical professional deems is necessary or is otherwise desired given their patient's health, circumstance, condition, or medical history. Since such additional steps are necessarily patient dependent, a discussion as to particular steps that should or should not be taken is omitted herein as being beyond the scope of the appended claims.

In another embodiment, if the hot spots are classified as being possibly malignant, an alert or a diagnostic report is generated. The alert may take the form of a message displayed on a display device or a sound activated at, for example, a nurse's station. The alert may take the form of a colored or blinking light which provides a visible indication that an alert condition exists. The alert can be a text, email, audio, phone call, and/or a video message. The alert may include images of the hot spots, and/or aspects of processing such as results of the measure of symmetry, interim values, and the like. The alert may be communicated to one or more remote devices over a wired or wireless network. The alert may be sent directly to a handheld wireless cellular device of a medical professional.

It should be understood that the flow diagrams depicted herein are illustrative. One or more of the operations illustrated in the flow diagrams may be performed in a differing order. Other operations may be added, modified, enhanced, or consolidated. Variations thereof are intended to fall within the scope of the appended claims. All or portions of the flow diagrams may be implemented partially or fully in hardware in conjunction with machine readable/executable program instructions.

Block Diagram of Image Processing System

Figure 8:
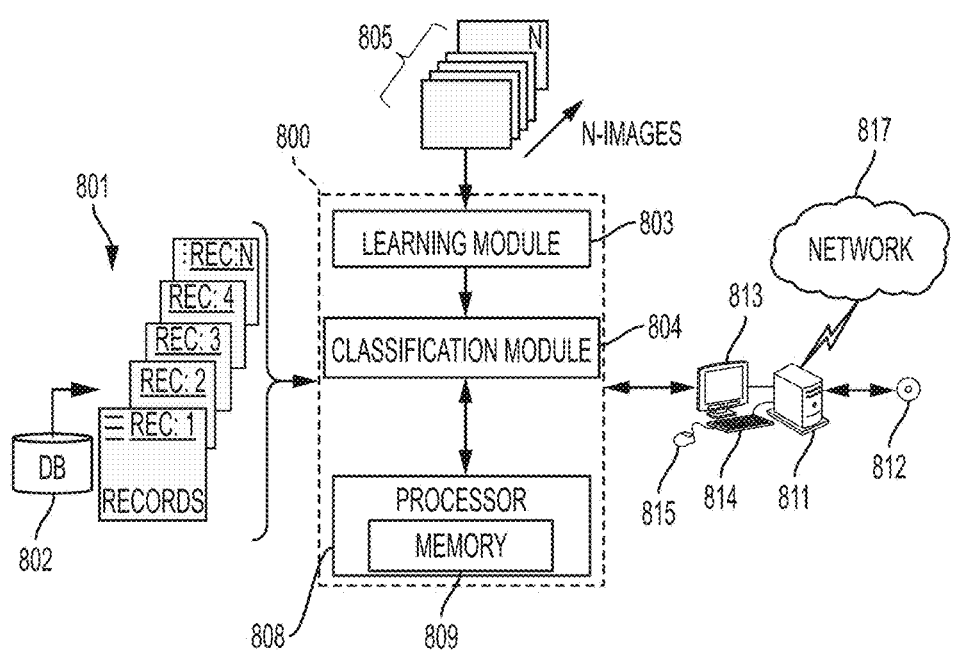
FIG. 8 shows a functional block diagram of one example image processing system for processing thermographic images for breast cancer screening in accordance with the embodiment described with respect to the flow diagram of FIG. 7.

Reference is now being made to FIG. 8 which shows a functional block diagram of one example image processing system for processing thermographic images for breast cancer screening in accordance with the embodiment described with respect to the flow diagram of FIG. 7.

A training set (collectively at 801) comprising records containing thermal images, hot spots, medical records of a plurality of patients, and the like, are retrieved from a database 802 comprising a storage device. Although the database is shown as an external device, the database may be internal to the workstation 811 mounted, for example, on a hard disk. The training set is provided to a classifier system 800. In the embodiment shown, the classifier system comprises a Learning Module 803 which processes the training set 801 such that the classifier system can determine an appropriate threshold for a measure of symmetry such that hot spots can be classified into at least a first and second class. Learning Module 803 may further be configured to prune the training set, as needed or as desired, such that the classifier is trained with data which meets a pre-determined criteria of acceptability, at least for accuracy such that false positives and false negatives are minimized. Once training has completed, Learning Module 803 signals the Processor 808 to receive a total of n thermal images of the left and right breast of a patient undergoing breast cancer screening in accordance with the methods disclosed herein (collectively at 805) where n≥1. It should be appreciated that the received thermal images 805 have been acquired by the imaging device 101 and represent thermographic images such as those in FIGS. 2 and 3. The thermographic images can be communicated directly to the classifier system 800 via wired or wireless pathways (not shown). Some or all of the functionality of the classifier system 800 may be integrated in the imaging device 101. Processor 808 retrieves machine readable program instructions from Memory 809 to analyze the thermographic image 805 to determine whether hot spots exist in each breast. If more than one hot spot is identified in each breast, a user can make a selection of a particular hot spot for processing using the graphical user interface of the workstation 811. If at least one hot spot is identified in each breast then the processor proceeds to extract at least one measure of symmetry from the hot spots. The measure of symmetry is then provided to a Classification Module 804 which receives the measure of symmetry and proceeds to classify the hot spots as being possibly malignant or non-malignant otherwise, using the threshold determined as a result of training.

System 800 is shown having been placed in communication with a workstation 811. A computer case of the workstation houses various components such as a motherboard with a processor and memory, a network card, a video card, a hard drive capable of reading/writing to machine readable media 812 such as a floppy disk, optical disk, CD-ROM, DVD, magnetic tape, and the like, and other software and hardware needed to perform the functionality of a computer workstation. The workstation further includes a display device 813, such as a CRT, LCD, or touch screen device, for displaying information, images, video, measurement data, computed measures of symmetry, medical information, results, interim values, and the like. A user can view any of that information and make a selection from menu options displayed thereon. Keyboard 814 and mouse 815 effectuate a user input. It should be appreciated that the workstation 811 has an operating system and other specialized software configured to display alphanumeric values, menus, scroll bars, dials, slideable bars, pull-down options, selectable buttons, and the like, for entering, selecting, modifying, and accepting information needed for processing in accordance with the teachings hereof. The workstation is further enabled to display thermal images, hot spots, and classifications as they are derived. The workstation can further display interim values, boundary conditions, and the like, in real-time as the Classification Module 804 performs its functionality. A user or technician may use the user interface of the workstation 811 to set parameters, view/adjust/delete values in the training set, and adjust various aspects of the classifier system as needed or as desired, depending on the implementation. Any of these selections or input may be stored/retrieved to storage device 812. Default settings can be retrieved from the storage device. A user of the workstation is also able to view or manipulate any of the records contained in the training set 801 via pathways not shown. The training set may be stored to a storage device internal to the workstation 811. Although shown as a desktop computer, the workstation 811 can be a laptop, mainframe, or a special purpose computer such as an ASIC, circuit, or the like. The embodiment of the workstation of FIG. 8 is illustrative and may include other functionality known in the arts.

Any of the components of the workstation may be placed in communication with the classifier system 800 or any devices in communication therewith. Any of the modules of the classifier system can be placed in communication with storage device 802 and/or computer readable media 812 and may store/retrieve there from data, variables, records, parameters, functions, and/or machine readable/executable program instructions, as needed to perform their intended functions. Each of the modules of the classifier system 800 may be placed in communication with one or more remote devices over network 817. It should be appreciated that some or all of the functionality performed by any of the modules or processing units of the system 800 can be performed, in whole or in part, by the workstation. The embodiment shown is illustrative and should not be viewed as limiting the scope of the appended claims strictly to that configuration. Various modules may designate one or more components which may, in turn, comprise software and/or hardware designed to perform the intended function.

The teachings hereof can be implemented in hardware or software using any known or later developed systems, structures, devices, and/or software by those skilled in the applicable art without undue experimentation from the functional description provided herein with a general knowledge of the relevant arts. One or more aspects of the methods described herein are intended to be incorporated in an article of manufacture which may be shipped, sold, leased, or otherwise provided separately either alone or as part of a product suite or a service. It will be appreciated that the above-disclosed and other features and functions, or alternatives thereof, may be desirably combined into other different systems or applications. Presently unforeseen or unanticipated alternatives, modifications, variations, or improvements may become apparent and/or subsequently made by those skilled in this art which are also intended to be encompassed by the following claims. The teachings of any publications referenced herein are hereby incorporated by reference in their entirety.

What is claimed is:

1. A method for breast cancer screening using a measure of symmetry extracted from a thermographic image of a left and right breast of a patient, the method comprising:
   receiving at least one thermographic image of a left and right breast of a patient;
   analyzing the thermographic image to determine whether a hot spot exists in each of a left breast and a right breast, a hot spot comprising a patch of pixels with an elevated temperature with respect to a temperature of pixels in surrounding tissue; and
   in response to a hot spot being identified in each breast, performing:
      extracting a measure of symmetry, wherein said extracting the measure of symmetry comprises
         binarizing the hot spots in each breast, with a value of 1 for pixels in the hot spots and a value of 0 for other pixels;
         convoluting the binary maps of the two breasts; and
         using a maximum value in the convolution as a measure of overlap area between the hot spots of the left and right breasts; and
      providing the overlap area as a measure of symmetry to a classifier system trained to classify an unclassified hot spot as being possibly malignant and non-malignant otherwise, based on a measure of symmetry.

2. The method of claim 1, wherein the hot spot inclusion of a given patch of pixels is based on one of: a mean temperature of pixels in the patch, a median temperature of pixels in the patch, and a highest temperature of pixels in the patch.

3. The method of claim 1, wherein, in response to more than one hot spot being identified in either the left or right breast, further comprising selecting one of the hot spots for malignancy analysis and reporting.

4. The method of claim 3, wherein in addition to the hot spot, one or more warm spots are identified as potential abnormal elements that require attention, wherein the potential abnormal elements comprise information for classifying the hot spot as possibly malignant.

5. The method of claim 1, wherein, in response to a hot spot being classified as possibly malignant or non-malignant, further comprising initiating an alert or a diagnostic report comprising any of: an audio message, a sound, a text message, sending an email, sending a text message, placing a phone call, playing a video, blinking a light, and wirelessly activating a remote device.

6. The method of claim 1, wherein the classifier system comprises any of: Support Vector Machine, a neural network, a Bayesian network, a Logistic regression, Naive Bayes, Randomized Forests, Decision Trees and Boosted Decision Trees, K-nearest neighbor, a Restricted Boltzmann Machine, and a hybrid system comprising any combination hereof.

7. The method of claim 1, further comprising updating a training set used to train the classifier system and improve the classifier system for classifying the hot spot.

8. The method of claim 1, further comprising communicating the classification to any of: a storage device, a display device, and a remote device over a network.

9. The method of claim 1, where the convolution is done with the temperature maps of the hot-spots of each breast with the rest of the pixels set to zero.

10. The method of claim 1, wherein said extracting the measure of symmetry further comprises
   binarizing the hot-spots in each breast, with a value of 1 for pixels in the hot spots and a value of 0 for other pixels;
   computing the area of hotspots as the number of pixels with a value of 1, separately for the left breast and right breast;
   determining the ratio of smaller hot spot area of one breast to the larger hot spot area in a contralateral breast; and providing the ratio of the areas as a measure of symmetry to a classifier system trained to classify an unclassified hot spot as being possibly malignant and non-malignant otherwise, based on the measure of symmetry.

11. A system for breast cancer screening using a measure of symmetry extracted from a thermographic image of a left and right breast of a patient, the system comprising:
  a storage device; and
  a processor in communication with the storage device, the processor retrieving executing machine readable program instructions which, when executed by the processor, enable the processor to:
    receive at least one thermographic image of a left and right breast of a patient;
    analyze the thermographic image to determine whether a hot spot exists in each of a left breast and a right breast, a hot spot comprising a patch of pixels with an elevated temperature with respect to a temperature of pixels in surrounding tissue; and
    in response to a hot spot being identified in each breast, performing:
      extract a measure of symmetry, wherein said extraction of the measure of symmetry comprises
        binarizing the hot-spots in each breast, with a value of 1 for pixels in the hot spots and a value of 0 for other pixels;
        convoluting the binary maps of the two breasts; and
        using a maximum value in the convolution as a measure of overlap area between the hot spots of the left and right breasts; and
      provide the overlap area as a measure of symmetry to a classifier system trained to classify an unclassified hot spot as being possibly malignant and non-malignant otherwise, based on a measure of symmetry.

12. The system of claim 11, wherein the hot spot inclusion of a given patch of pixels is based on one of: a mean temperature of pixels in the patch, a median temperature of pixels in the patch, and a highest temperature of pixels in the patch.

13. The system of claim 11, wherein, in response to more than one hot spot being identified in either the left or right breast, the processor further being configured to select one of the hot spots for malignancy analysis and reporting.

14. The system of claim 13, wherein in addition to the hot spot, one or more warm spots are identified as potential abnormal elements that require attention, wherein the potential abnormal elements comprise information for classifying the hot spot as possibly malignant.

15. The system of claim 11, wherein, in response to a hot spot being classified as possibly malignant or non-malignant, the processor further configured to initiate an alert or a diagnostic report comprising any of: an audio message, a sound, a text message, sending an email, sending a text message, placing a phone call, playing a video, blinking a light, and wirelessly activating a remote device.

16. The system of claim 11, wherein the classifier system comprises any of: Support Vector Machine, a neural network, a Bayesian network, a Logistic regression, Naïve Bayes, Randomized Forests, Decision Trees and Boosted Decision Trees, K-nearest neighbor, a Restricted Boltzmann Machine, and a hybrid system comprising any combination hereof.

17. The system of claim 11, wherein the processor is further configured to update a training set used to train the classifier system and to improve the classifier system for classifying the hot spot.

18. The system of claim 11, wherein the processor is further configured to communicate the classification to any of: a storage device, a display device, and a remote device over a network.

19. A method for breast cancer screening using a measure of symmetry extracted from a thermographic image of a left and right breast of a patient, the method comprising:
  receiving at least one thermographic image of a left and right breast of a patient;
  analyzing the thermographic image to determine whether a hot spot exists in each of a left breast and a right breast, a hot spot comprising a patch of pixels with an elevated temperature with respect to a temperature of pixels in surrounding tissue; and
  in response to a hot spot being identified in each breast, performing:
    extracting a measure of symmetry, wherein said extracting the measure of symmetry comprises
      binarizing the hot-spots in each breast, with a value of 1 for pixels in the hot spots and a value of 0 for other pixels;
      computing the area of hotspots as the number of pixels with a value of 1, separately for the left breast and right breast; and
      determining the ratio of smaller hot spot area of one breast to the larger hot spot area in a contralateral breast; and
    providing the ratio of the areas as a measure of symmetry to a classifier system trained to classify an unclassified hot spot as being possibly malignant and non-malignant otherwise, based on the measure of symmetry.

* * * * *